(12) United States Patent
Pekar et al.

(10) Patent No.: US 10,674,999 B2
(45) Date of Patent: Jun. 9, 2020

(54) ULTRASOUND SYSTEM AND METHOD

(71) Applicant: KONINKLIJKE PHILIPS N.V., Eindhoven (NL)

(72) Inventors: Martin Pekar, Eindhoven (NL); Martinus Bernardus Van Der Mark, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 367 days.

(21) Appl. No.: 15/527,890

(22) PCT Filed: Nov. 20, 2015

(86) PCT No.: PCT/EP2015/077291
§ 371 (c)(1),
(2) Date: May 18, 2017

(87) PCT Pub. No.: WO2016/083273
PCT Pub. Date: Jun. 2, 2016

(65) Prior Publication Data
US 2018/0325491 A1     Nov. 15, 2018

(30) Foreign Application Priority Data
Nov. 25, 2014   (EP) .................................... 14194623

(51) Int. Cl.
*A61B 8/02*      (2006.01)
*A61B 8/00*      (2006.01)
(Continued)

(52) U.S. Cl.
CPC .......... *A61B 8/4494* (2013.01); *A61B 8/4444* (2013.01); *A61B 8/4483* (2013.01);
(Continued)

(58) Field of Classification Search
CPC ....... A61B 8/00; A61B 8/4444; A61B 8/4483; A61B 8/4494; A61B 8/54; A61N 7/00;
(Continued)

(56) References Cited

U.S. PATENT DOCUMENTS 5,997,479 A    12/1999  Savord et al.
6,013,032 A     1/2000  Savord et al.
(Continued)

FOREIGN PATENT DOCUMENTS

JP    2007527285 A    9/2007
JP    2009182838 A    8/2009
(Continued)

OTHER PUBLICATIONS

Kim et al "An Experimental Study on Coded Excitation in CMUT Arrays to Utilize Simultaneous Transmisison Multiple-Zone Focusing Method with Frequency Divided Sub-band Chirps" Proc. IEEE Ultrasonics Symp. 2013, pp. 1428-1431.
(Continued)

*Primary Examiner* — Hovhannes Baghdasaryan
*Assistant Examiner* — Amie M Ndure

(57) ABSTRACT

An ultrasound system (1) is disclosed that comprises a probe (10) including an array (110) of CMUT (capacitive micromachined ultrasound transducer) cells (100), each cell comprising a substrate (112) carrying a first electrode (122), the substrate being spatially separated from a flexible membrane (114) including a second electrode (120) by a gap (118); and a bias voltage source (45) coupled to said probe and adapted to provide the respective first electrodes and second electrodes of at least some of the CMUT cells with a monotonically varying bias voltage including a monotonically varying frequency modulation in a transmission mode of said probe such that the CMUT cells are operated in a collapsed state and transmit at least one chirped pulse during said trans-
(Continued)

mission mode. Such a system for instance may be an ultrasound imaging system or an ultrasound therapeutic system. An ultrasonic pulse generation method using such as system is also disclosed.

15 Claims, 9 Drawing Sheets

(51) Int. Cl.

| | | |
|---|---|---|
| *B06B 1/02* | (2006.01) | |
| *G01S 15/89* | (2006.01) | |
| *A61N 7/00* | (2006.01) | |
| *G01N 29/24* | (2006.01) | |
| *G01S 7/52* | (2006.01) | |

(52) U.S. Cl.
CPC .............. *A61N 7/00* (2013.01); *B06B 1/0215* (2013.01); *B06B 1/0292* (2013.01); *G01N 29/2406* (2013.01); *G01S 15/8954* (2013.01); *A61B 8/54* (2013.01); *B06B 2201/51* (2013.01); *G01S 7/5208* (2013.01); *G01S 7/52038* (2013.01); *G01S 15/8915* (2013.01)

(58) Field of Classification Search
CPC ....... B06B 1/02; B06B 1/0292; B06B 1/0215; B06B 2201/51; G01N 29/24; G01N 29/2406; G01S 15/8954; G01S 15/8915; G01S 7/5208; G01S 7/52038
See application file for complete search history.

(56) References Cited

U.S. PATENT DOCUMENTS

| | | | |
|---|---|---|---|
| 6,283,919 B1 | 9/2001 | Roundhill et al. | |
| 6,328,697 B1 | 12/2001 | Fraser | |
| 6,443,896 B1 | 9/2002 | Detmer | |
| 6,458,083 B1 | 10/2002 | Jago et al. | |
| 6,530,885 B1 | 3/2003 | Entrekin et al. | |
| 6,623,432 B2 | 9/2003 | Powers et al. | |
| 2003/0048698 A1* | 3/2003 | Barnes ................ | G01S 7/52038 367/181 |
| 2004/0236223 A1* | 11/2004 | Barnes ................ | A61B 5/0048 600/459 |
| 2005/0075572 A1* | 4/2005 | Mills ................... | B06B 1/0292 600/459 |
| 2005/0119575 A1* | 6/2005 | Ladabaum ........... | B06B 1/0292 600/459 |
| 2005/0200241 A1* | 9/2005 | Degertekin .......... | B06B 1/0292 310/334 |
| 2005/0219953 A1* | 10/2005 | Bayram ................ | B06B 1/0292 367/178 |
| 2005/0225916 A1* | 10/2005 | Bolorforosh ........ | G01S 7/52017 361/91.1 |
| 2009/0250729 A1* | 10/2009 | Lemmerhirt ............. | A61B 8/00 257/254 |
| 2009/0299192 A1* | 12/2009 | Asafusa ................ | B06B 1/0292 600/459 |
| 2011/0163630 A1 | 7/2011 | Klootwijk et al. | |

FOREIGN PATENT DOCUMENTS

| | | |
|---|---|---|
| JP | 2009279033 A | 12/2009 |
| WO | 2005084284 A2 | 9/2005 |
| WO | 2009096576 A2 | 8/2009 |

OTHER PUBLICATIONS

O.Oralkan et al: "Experimental characterization of collapse-mode CMUT operation",IEEE Transactions On Ultras0nics,Ferr0electrics and Frequency Control,vol. 53, No. 8, Aug. 1, 2006 (Aug. 1, 2006) pp. 1513-1523.

Misaridis T et al: "Use of modulated excitation signals in medical ultrasound.Part I: basic concepts and expected benefits",IEEE Transactions on Ultrasonics,Ferroelectrics and Frequency Control, IEEE, US,vol. 52, No. 2,Feb. 1, 2005 (Feb. 1, 2005), pp. 177-191.

Park K K et al: "Comparison of conventional and collapse-mode CMUT in 1-D array configuration". Ultrasonics Symposium (IUS), 2011 IEEE International, IEEE,Oct. 18, 2011 (Oct. 18, 2011), pp. 1000-1003.

Aydo Du Elif et al: "Parametric nonlinear lumped element model for circular CMUTs in collapsed mode", IEEE Transactions on Ultrasonics,Ferroelectrics and Frequency Control,IEEE, US, vol. 61, No. 1,Jan. 1, 2014 (Jan. 1, 2014), pp. 173-181.

Varrary et al "A Multi-Frequency Approach to Increase the Native Resolution of Ultrasound Images" 20th European Signal Processing Conference Aug. 27-31, 2012.

Legros et al "Tissue Harmonic Imaging with CMUTs" , IEEE International Ultrasonics Symposium Proceedings 2011.

Plastic Material's acoustic Properties, pp. 2-3, 2014 downloaded from www.ndt.net/links/proper.htm.

Y. Sun, D. E. Kruse, and K. W. Ferrara, "Contrast imaging with chirped excitation.," IEEE Trans. Ultrason. Ferroelectr. Freq. Control, vol. 54, No. 3, pp. 520-529, Mar. 2007.

G. Gurun, C. Tekes, J. Zahorian, T. Xu, S. Satir, M. Karaman, J. Hasler, and F. L. Degertekin, "Single-Chip CMUT-on-CMOS Front-End System for Real-Time Volumetric IVUS and ICE Imaging," vol. 61, No. 2, 2014.

A. E. Siegman, "Lasers,", Chapter 9. Mill Valley: University Science Books, 1986.

P. He, "Measurement of acoustic dispersion using both transmitted and reflected pulses," J. Acoust. Soc. Am., vol. 107, No. 2, pp. 801-807, Feb. 2000.

\* cited by examiner

ULTRASOUND SYSTEM AND METHOD

This application is the U.S. National Phase application under 35 U.S.C. § 371 of International Application No. PCT/EP2015/077291, filed on Nov. 20, 2015, which claims the benefit of EP Application Serial No. 14194623.6 filed Nov. 25, 2014. These applications are hereby incorporated by reference herein.

FIELD OF THE INVENTION

The present invention relates to an ultrasound system such as an ultrasound diagnostic imaging system or an ultrasound therapeutic system comprising a probe including an array of CMUT (capacitive micromachined ultrasound transducer) cells, each cell comprising a substrate carrying a first electrode, the substrate being spatially separated from a flexible membrane including a second electrode by a gap; and a voltage source coupled to said probe.

The present invention further relates to an ultrasonic imaging method using such a system.

BACKGROUND OF THE INVENTION

Ultrasonic transducers used for medical imaging have numerous characteristics that lead to the production of high quality diagnostic images. Among these are broad bandwidth, affecting resolution and high sensitivity, which combined with pressure output affects depth of field, to low level acoustic signals at ultrasonic frequencies. Conventionally the piezoelectric materials which possess these characteristics have been made of PZT and PVDF materials, with PZT being particularly popular as the material of choice. However, PZT suffers from a number of notable drawbacks. Firstly, the ceramic PZT materials require manufacturing processes including dicing, matching layer bonding, fillers, electroplating and interconnections that are distinctly different and complex and require extensive handling, all of which can result in transducer stack unit yields that are lower than desired. This manufacturing complexity increases the cost of the final transducer probe and puts design limitations on the minimum spacing between the elements as well as the size of the individual elements. Moreover, PZT materials have a poorly matched impedance to water or biological tissue, such that matching layers need to be added to the PZT materials in order to obtain the desired acoustic impedance matching with the medium of interest.

As ultrasound system mainframes have become smaller and dominated by field programmable gate arrays (FPGAs) and software for much of the signal processing functionality, the cost of system mainframes has dropped with the size of the systems. Ultrasound systems are now available in inexpensive portable, desktop and handheld form, for instance for use as ultrasound diagnostic imaging systems or as ultrasound therapeutic systems in which a particular (tissue) anomaly is ablated using high-energy ultrasound pulses. As a result, the cost of the transducer probe is an ever-increasing percentage of the overall cost of the system, an increase which has been accelerated by the advent of higher element-count arrays used for 3D imaging in the case of ultrasound diagnostic imaging systems. The probes used for ultrasound 3D imaging with electronic steering rely on specialized semiconductor devices application-specific integrated circuits (ASICs) which perform microbeam forming for two-dimensional (2D) arrays of transducer elements. Accordingly it is desirable to be able to manufacture transducer arrays with improved yields and at lower cost to facilitate the need for low-cost ultrasound systems, and preferably by manufacturing processes compatible with semiconductor production.

Recent developments have led to the prospect that medical ultrasound transducers can be batch manufactured by semiconductor processes. Desirably these processes should be the same ones used to produce the ASIC circuitry needed by an ultrasound probe such as a CMOS process. These developments have produced micromachined ultrasonic transducers or MUTs, the preferred form being the capacitive MUT (CMUT). CMUT transducers are tiny diaphragm-like devices with electrodes that convert the sound vibration of a received ultrasound signal into a modulated capacitance. For transmission the capacitive charge applied to the electrodes is modulated to vibrate/move the diaphragm of the device and thereby transmit an ultrasound wave. Since these diaphragms are manufactured by semiconductor processes the devices generally have dimensions in the 10-500 micrometer range, with spacing between the individual diaphragms less than a few micrometers. Many such individual CMUTs can be connected together and operated in unison as a single transducer element. For example, four to sixteen CMUTs can be coupled together to function in unison as a single transducer element. A typical 2D transducer array can have 2000-3000 CMUT transducer elements.

The manufacture of CMUT transducer-based ultrasound systems is therefore more cost-effective compared to PZT-based systems. Moreover, due to the materials used in such semiconductor processes, the CMUT transducers exhibit much improved acoustic impedance matching to water and biological tissue, which obviates the need for a matching layer and yields an improved effective bandwidth.

One of the main challenges in developing effective ultrasound systems, and in particular CMUT transducer-based ultrasound systems is to provide systems with excellent image resolution and good depth-of-field in case of an ultrasound diagnostic imaging system. These are conflicting requirements, as higher frequency pulsed ultrasound leads to improved resolution but shorter depth-of-field due to the frequency dependent attenuation of the medium. In order to obtain high resolution in depth, high pressure short pulses are desired which require a large bandwidth. Although in principle CMUT transducers can generate a broad spectrum of frequencies the bandwidth is limited because the frequency at which they operate efficiently depends strongly on the applied static bias voltage over the CMUT.

B.-H. Kim et al., "An Experimental Study on Coded Excitation in CMUT Arrays to Utilize Simultaneous Transmission Multiple-zone Focusing Method with Frequency Divided Sub-band Chirps," in Proc. IEEE Ultrasonics Symp., 2013, pp. 1428-1431 disclose the transmission of chirped ultrasound pulses with a CMUT array. However, such pulses exhibit relatively narrow effective bandwidths due to the loss of acoustic performance throughout the bandwidth range and as such are of limited use when trying to improve resolution and/or depth-of-field of the imaging data, for which the acoustical performance should be maintained over an as large as possible bandwidth.

SUMMARY OF THE INVENTION

The present invention seeks to provide an ultrasound system having a CMUT transducer-based probe exhibiting improved bandwidth and pressure output characteristics.

The present invention further seeks to provide a method of generating ultrasound pulses with such an ultrasound diagnostic imaging system.

According to an aspect, there is provided an ultrasound system comprising a probe including an array of CMUT (capacitive micromachined ultrasound transducer) cells, each cell comprising a substrate carrying a first electrode, the substrate being spatially separated from a flexible membrane including a second electrode by a gap; and a voltage source coupled to said probe and adapted to provide the respective first electrodes and second electrodes of at least some of the CMUT cells with a monotonically varying voltage including a monotonically varying frequency modulation in a transmission mode of said probe such that the CMUT cells are operated in a collapsed state and transmit at least one chirped pulse during said transmission mode.

The present inventors have realized that by driving the CMUT cells into their collapsed state during pulse transmission and generating a chirped pulse by varying the voltage and frequency modulation in a correlated manner, the acoustic pressure output of the CMUT cells can be maintained over an increased frequency range, thereby improving the effective bandwidth at which the transducer array is operated.

In an embodiment, the voltage source comprises a first stage adapted to generate a static component of said voltage during said transmission mode, wherein the static component is sufficient to force the CMUT cells in the collapsed state; and a second stage adapted to generate a monotonically varying component of said voltage, said monotonically varying component including the monotonically varying frequency modulation, and wherein the voltage source is adapted to combine the static component and the monotonically varying component to form the monotonically varying voltage including a monotonically varying frequency modulation. This has the advantage that the bulk of the voltage does not have to follow the relatively rapid modulation such that it can be produced using a voltage generator including large smoothing resistors, thereby reducing the amount of noise in the overall voltage signal.

The monotonically varying voltage and the monotonically varying frequency modulation may be monotonically increasing, e.g. continuously increasing. This has the advantage that lower frequency components of the chirped pulse or pulse train are generated first in time, which for instance facilitates the compression of the chirped pulse using a dispersive medium in applications where a chirped pulse is undesirable, e.g. high-resolution ultrasound imaging. A chirped pulse formed by the monotonically increasing voltage and frequency modulation for instance can be compressed using common materials as many of such materials exhibit anomalous dispersion for ultrasound frequencies. Low-density polyethylene and polyether ether ketone (PEEK) are particularly suitable examples of such materials.

However, it is feasible to provide engineered materials, e.g. composite materials comprising weakly scattering elements such as fibers, carbon nanotubes, particles and so on that strongly influence either the bulk modulus or density of the composite, metamaterials that can have an acoustic band gap close to which the velocity dispersion is varying strongly, MEMS windows, wherein the properties of the engineered materials, e.g. composition, stiffness, thickness and so on, are controlled to provide the material with the desired material properties, e.g. normal dispersion of (certain) ultrasound frequency bands, in which case the monotonically varying voltage and the monotonically varying frequency modulation may be monotonically decreasing, e.g. continuously decreasing for compression by a material comprising normal dispersion characteristics for the frequencies of the ultrasound pulse.

Preferably, the monotonically varying frequency modulation is matched to monotonic variations in the resonance frequency of the respective membranes of the CMUT cells induced by the applied monotonically varying bias voltage. This ensures that the frequency applied to the CMUT cells is matched to their resonance frequencies, which ensures that the acoustic performance at that resonance frequency is optimized. It is noted that for constant voltages applied throughout a transmission cycle the CMUT cells are typically operated at a static resonance frequency, i.e. the resonance frequency induced by the constant voltage, which limits the effective bandwidth due to reduced acoustic performance for generated frequency components that are substantially different to the static resonance frequency.

The frequency modulation may be a linearly increasing frequency modulation, as this is compatible with first order dispersion compensation. This may be combined with a non-linearly increasing voltage in order to optimize acoustic output.

In an embodiment, the ultrasound diagnostic system further comprises a plate of a dispersive material in front of the array of CMUT cells for compressing said chirp. This for instance is desirable if the ultrasound diagnostic system is used for high-resolution ultrasound imaging, in which short pulses with large spectral bandwidths are desired for optimal resolution.

The plate may be removably mounted in front of said array such that the ultrasound diagnostic system may be configured to operate in application domains in which chirped pulses are undesirable, e.g. high-resolution imaging, and application domains in which chirped pulses are desirable, e.g. ultrasound harmonic imaging or contrast imaging.

The thickness of the plate may be matched to the chirp characteristics of the chirped pulse or pulse train in order to minimize the pulse width of the compressed pulse or pulse train. In embodiments in which a transmitting CMUT cell is also used as a receiver channel, the plate may have a thickness of half the optimum thickness for said compression such that the pulse is fully compressed after the second passage through the plate, i.e. when returning as a pulse echo.

Any suitable dispersive material may be used for the dispersive plate, as explained above.

Preferably, the at least one chirped pulse has a duration ranging from 0.1-1.0 microsecond as this yields particularly good imaging results in diagnostic imaging applications. When applied in therapeutic applications, a longer optimal pulse width may be applicable.

In an embodiment, the voltage source is further adapted to provide the respective first electrodes and second electrodes of at least some of the CMUT cells with a further voltage that forces the CMUT cells in the collapsed state during a reception mode of said probe. A monotonically varying voltage, e.g. a continually decreasing voltage may be used in order to sweep the frequency range of the echo of the chirped pulse or pulse train generated in the transmission mode. This for instance may facilitate detection of a chirped echo at optimal sensitivity, i.e. by collapsing the CMUT cell to a degree where its corresponding resonance frequency matches the frequency of the expected echo signal, as the high frequency components of such an echo typically arrive first in time due to the limited penetration depth of the high frequency components of the ultrasound pulse or pulse train into the medium.

The ultrasound diagnostic system may further comprise a user interface, wherein the voltage source is adapted to provide the further voltage as defined by a user using said user interface during the reception mode in order to facilitate a user to set the voltage to a desired mode of operation of the system.

According to another aspect, there is provided a method of generating ultrasound pulses, comprising providing an array of CMUT (capacitive micromachined ultrasound transducer) cells, each cell comprising a substrate carrying a first electrode, the substrate being spatially separated from a flexible membrane including a second electrode by a gap; and providing, in a transmission mode, the respective first and second electrodes of at least some of the CMUT cells with a monotonically varying voltage including a monotonically varying frequency modulation such that the CMUT cells are operated in a collapsed state and transmit at least one chirped pulse. This produces a pulse or pulse train having the desired acoustic performance over a greater frequency range, which for instance improves the imaging resolution of the ultrasound images produced with such pulses when applied in an ultrasound imaging system or improves the peak power of a chirped pulse delivered to a tissue for therapeutic treatment with an ultrasound therapeutic system, for instance by matching the chirp of the pulse with the dispersive properties of the tissue path along which the pulse has to travel before reaching an anomaly, such that the tissue path acts as the pulse compression medium in such a manner that the pulse achieves (near-) optimal compression at the location of the anomaly, such that the pulse energy is condensed in time and the peak power of the pulse is increased as a result.

The method may further comprise transmitting the at least one chirped pulse through a dispersive material to compress the at least one chirped pulse to obtain a narrow pulse containing a wide range of frequencies, which facilitates good resolution imaging, e.g. in high-resolution imaging applications.

The method may further comprise providing, in a reception mode, the respective first and second electrodes of at least some of the CMUT cells with a further voltage forcing the CMUT cells in the collapsed state. The further voltage may be a monotonically varying voltage such as a continuously decreasing voltage in order to emphasize received ultrasound echoes emanating from different field depths, e.g. for obtaining high-resolution 3D ultrasound images.

BRIEF DESCRIPTION OF THE DRAWINGS

Embodiments of the invention are described in more detail and by way of non-limiting examples with reference to the accompanying drawings, wherein FIG. 1 schematically depicts a CMUT cell of an ultrasound system according to an embodiment.

DETAILED DESCRIPTION OF THE EMBODIMENTS

Figure 1:
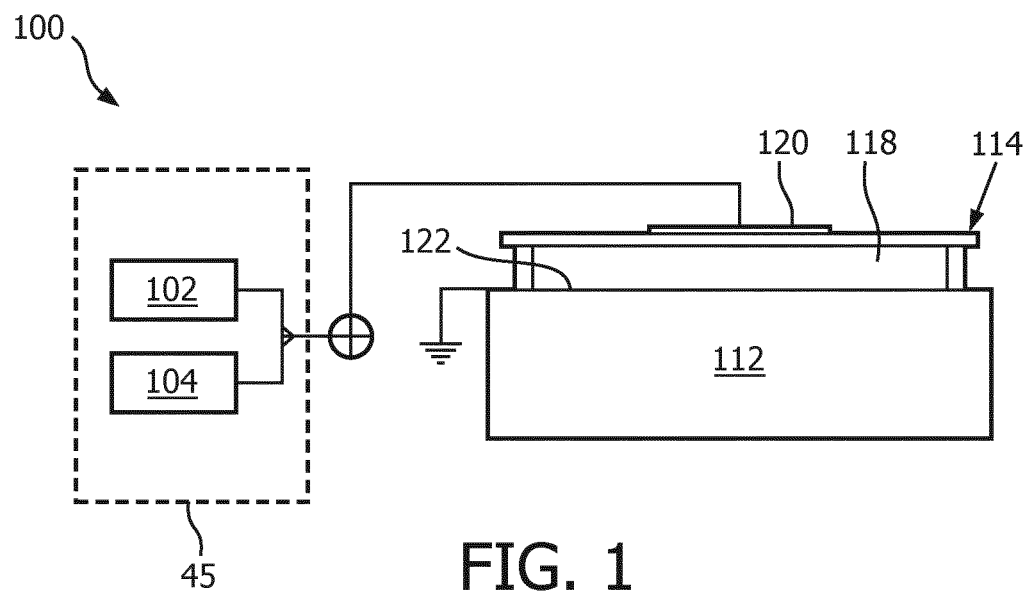

It should be understood that the Figures are merely schematic and are not drawn to scale. It should also be understood that the same reference numerals are used throughout the Figures to indicate the same or similar parts.

FIG. 1 shows an aspect of an ultrasound system according to an embodiment, in which the system includes an ultrasound probe having a transducer array comprising CMUT cells 100. As will be explained in further detail below, such an ultrasound system may be an ultrasound diagnostic imaging system in some embodiments or may be an ultrasound therapeutic system in some other embodiments. The present invention is not limited to a particular type of CMUT cells such that any suitable design of CMUT cell 100 may be contemplated. Such a CMUT cell 100 typically comprises a membrane or diaphragm 114 suspended above a silicon substrate 112 with a gap or cavity 118 there between. A top electrode 120 is located on the diaphragm 114 and moves with the diaphragm. A bottom electrode is located on the floor of the cell on the upper surface of the substrate 112 in this example. Other realizations of the electrode 120 design can be considered, such as electrode 120 may be embedded in the membrane 114 or it may be deposited on the membrane 114 as an additional layer. In this example, the bottom electrode 122 is circularly configured and embedded in the substrate layer 112 by way of non-limiting example. Other suitable arrangements, e.g. other electrode shapes and other locations of the bottom electrode 122, e.g. on the substrate layer 112 such that the bottom electrode 112 is directly exposed to the gap 118 or separated from the gap 118 by an electrically insulating layer or film to prevent a short-circuit between the top electrode 120 and the bottom electrode 122. In addition, the membrane layer 114 is fixed relative to the top face of the substrate layer 112 and configured and dimensioned so as to define a spherical or cylindrical cavity 118 between the membrane layer 114 and the substrate layer 112. It is noted for the avoidance of doubt that in FIG. 1 the bottom electrode 122 is grounded by way of non-limiting example. Other arrangements, e.g. a grounded top electrode 120 or both top electrode 120 and bottom electrode 122 floating are of course equally feasible.

The cell 100 and its cavity 118 may exhibit alternative geometries. For example, cavity 118 could exhibit a rectangular or square cross-section, a hexagonal cross-section, an elliptical cross-section, or an irregular cross-section. Herein, reference to the diameter of the CMUT cell 100 shall be understood as the biggest lateral dimension of the cell.

In an embodiment, the bottom electrode 122 is insulated on its cavity-facing surface with an additional layer (not pictured). A preferred electrically insulating layer is an oxide-nitride-oxide (ONO) dielectric layer formed above the substrate electrode 122 and below the membrane electrode 120 although it should be understood any electrically insulating material may be contemplated for this layer. The ONO-dielectric layer advantageously reduces charge accumulation on the electrodes which leads to device instability and drift and reduction in acoustic output pressure.

An example fabrication of ONO-dielectric layers on a CMUT is discussed in detail in European patent application EP 2,326,432 A2 by Klootwijk et al., filed Sep. 16, 2008 and entitled "Capacitive micromachined ultrasound transducer." Use of the ONO-dielectric layer is desirable with pre-collapsed CMUTs, which are more susceptible to charge retention than CMUTs operated with suspended membranes. The disclosed components may be fabricated from CMOS compatible materials, e.g., Al, Ti, nitrides (e.g., silicon nitride), oxides (various grades), tetra ethyl oxysilane (TEOS), poly-silicon and the like. In a CMOS fabrication, for example, the oxide and nitride layers may be formed by chemical vapor deposition and the metallization (electrode) layer put down by a sputtering process.

Suitable CMOS processes are LPCVD and PECVD, the latter having a relatively low operating temperature of less than 400° C. Exemplary techniques for producing the disclosed cavity 118 involve defining the cavity in an initial portion of the membrane layer 114 before adding a top face of the membrane layer 114. Other fabrication details may be found in U.S. Pat. No. 6,328,697 (Fraser). In the exemplary embodiment depicted in FIG. 1, the diameter of the cylindrical cavity 118 is larger than the diameter of the circularly configured electrode plate 122. Electrode 120 may have the same outer diameter as the circularly configured electrode plate 122, although such conformance is not required. Thus, in an exemplary implementation of the present invention, the membrane electrode 120 is fixed relative to the top face of the membrane layer 114 so as to align with the electrode plate 122 below. The electrodes of the CMUT provide the capacitive plates of the device and the gap 118 is the dielectric between the plates of the capacitor. When the diaphragm vibrates, the changing dimension of the dielectric gap between the plates provides a changing capacitance which is sensed as the response of the CMUT to a received acoustic echo. The spacing between the electrodes is controlled by applying a static voltage, e.g. a DC bias voltage, to the electrodes with a voltage circuit 45. As is known per se, by applying a static voltage above a certain threshold, the CMUT cell 100 is forced into a collapsed state in which the membrane 114 collapses onto the substrate 112. This threshold value may depend on the exact design of the CMUT cell 100 and is defined as the DC bias voltage at which the membrane 114 sticks to (contacts) the cell floor by Vander-Waals force during the application of the bias voltage. The amount (area) of contact between the membrane 114 and the substrate 112 is dependent on the applied bias voltage. Increasing the contact area between the membrane 114 and the substrate 112 increases the resonance frequency of the membrane 114, as will be explained in more detail with the aid of FIG. 2a and FIG. 3a.

Figure 2A:
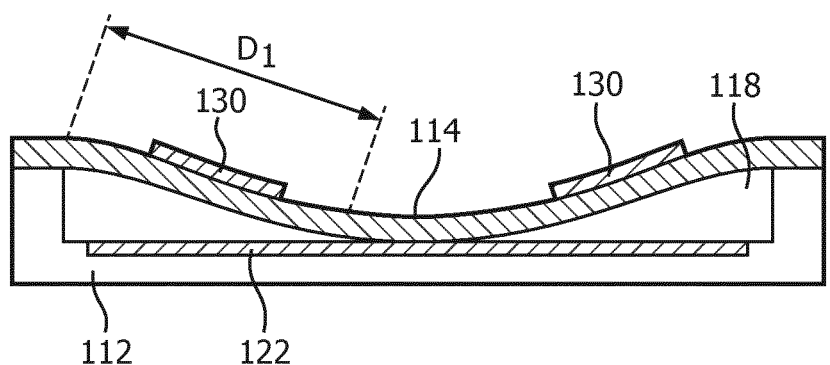
FIGS. 2A, 2B, 3A and 3B depict operating principles of such a CMUT cell.

The frequency response of a collapsed mode CMUT cell 100 may be varied by adjusting the DC bias voltage applied to the CMUT electrodes after collapse. As a result, the resonant frequency of the CMUT cell increases as a higher DC bias voltage is applied to the electrodes. The principles behind this phenomenon are illustrated in FIGS. 2a, 2b, 3a and 3b. The cross-sectional views of FIGS. 2a and 3a illustrate this one-dimensionally by the distances D1 and D2 between the outer support of the membrane 114 and the point where the membrane begins to touch the floor of the cavity 118 in each illustration. It can be seen that the distance D1 is a relatively long distance in FIG. 2a when a relatively low bias voltage is applied, whereas the distance D2 in FIG. 3a is a much shorter distance due to a higher bias voltage being applied. These distances can be compared to long and short strings which are held by the ends and then plucked. The long, relaxed string will vibrate at a much lower frequency when plucked than will the shorter, tighter string. Analogously, the resonant frequency of the CMUT cell in FIG. 2a will be lower than the resonant frequency of the CMUT cell in FIG. 3a which is subject to the higher pulldown bias voltage.

Figure 2B:
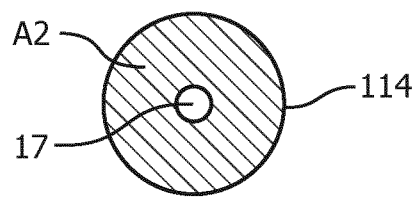
Figure 3A:
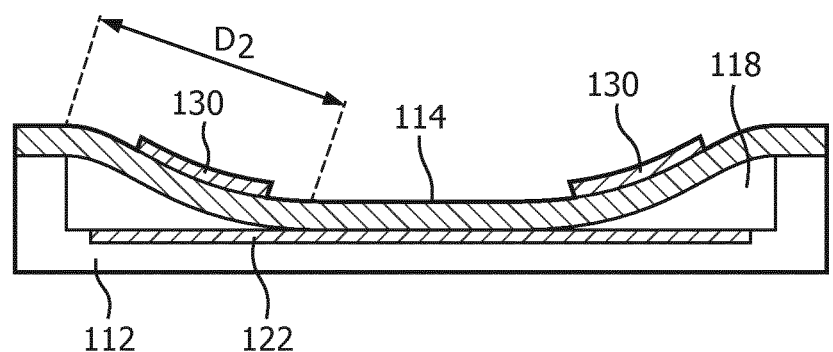
Figure 3B:
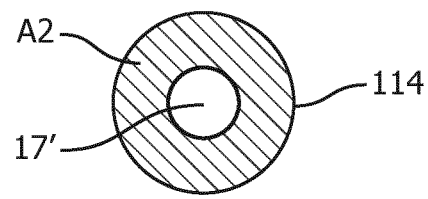

The phenomenon can also be appreciated from the two dimensional illustrations of FIGS. 2b and 3b, as it is in actuality a function of the effective operating area of the CMUT membrane. When the membrane 114 just touches the floor of the CMUT cell as shown in FIG. 2a, the effective vibrating area A1 of the non-contacting (free vibrating) portion of the cell membrane 114 is large as shown in FIG. 2b. The small hole in the center 17 represents the center contact region of the membrane. The large area membrane will vibrate at a relatively low frequency. This area 17 is an area of the membrane 114, which is collapsed to the floor of the CMUT cell. But when the membrane is pulled into deeper collapse by a higher bias voltage as in FIG. 3a, the greater central contact area 17' results in a lesser free vibrating area A2 as shown in FIG. 3b. This lesser area A2 will vibrate at a higher frequency than the larger A1 area. Thus, as the DC bias voltage is decreased the frequency response of the collapsed CMUT cell decreases, and when the DC bias voltage increases the frequency response of the collapsed CMUT cell increases.

Figure 4:
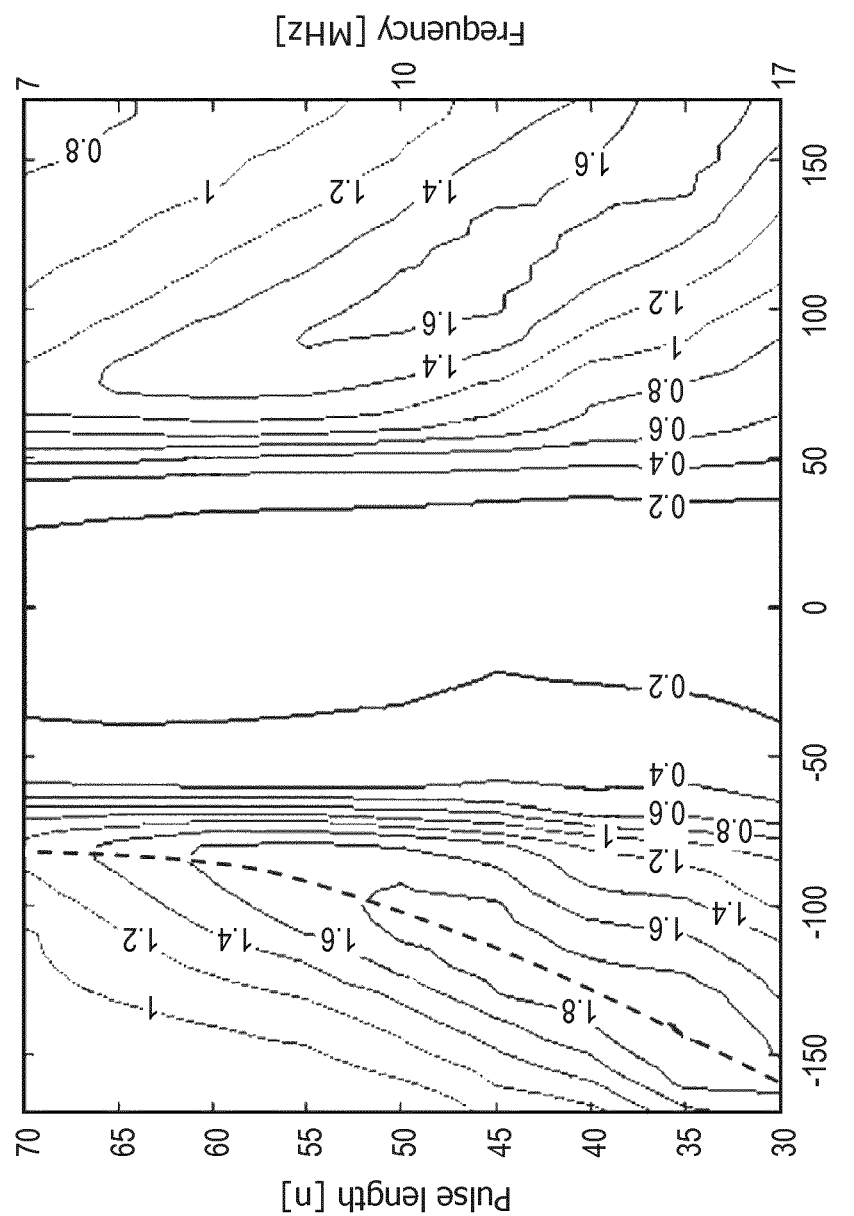
FIG. 4 is a contour plot of the acoustical performance of such a CMUT cell.

An important insight on which aspects of the present invention are based is depicted in FIG. 4, which shows a contour plot of the acoustical pressure output of a typical CMUT cell 100 in collapse mode as a function of applied DC bias voltage with an AC modulation or frequency modulation of constant frequency during transmission. The corresponding pulse length is half the applied frequency. As can be seen from this contour plot, when the CMUT cell 100 is operated at a fixed or static voltage, e.g. a DC bias voltage of static value, optimal acoustic performance is obtained for a small range of frequencies only. However, when varying the bias voltage and the frequency modulation on the bias voltage signal in a correlated manner, as indicated by the dashed line in the contour plot, the optimal acoustic performance of the CMUT cell 100 may be achieved over a much larger frequency range, thereby increasing the effective bandwidth of the ultrasound pulse (or pulse train) generated in the transmission mode of the ultrasound probe including the CMUT cell 100.

This can be understood in back reference to FIGS. 2a and 3a, which explained that the resonance frequency of the CMUT cell 100 in a collapsed state is a function of the applied (DC) bias voltage. By sweeping the applied voltage, a spectrum of resonance frequencies is generated, for which the RF component, i.e. the frequency modulation, of the applied voltage is also swept such that the frequency of this modulation matches, or at least closely resembles, the resonance frequency of the membrane 114 corresponding to the applied DC bias voltage. In this manner, a chirped pulse or pulse train can be generated in which all spectral components induce (near-)optimal acoustic performance of the CMUT cell 100. This therefore ensures (near-)optimal imaging resolution over a large bandwidth of the imaging spectrum.

Therefore, in accordance with an aspect of the present invention, the voltage source 45 is adapted to, in a transmission mode of the ultrasound diagnostic imaging system, provide the first electrodes 120 and second electrodes 122 of the CMUT cells 100 used for the transmission of the ultrasound imaging pulse(s) with a monotonically varying voltage including a monotonically varying frequency modulation in a transmission mode of said probe such that these CMUT cells 100 are operated in a collapsed state and transmit at least one chirped pulse.

In the context of the present application, a monotonically varying voltage may mean a continuously increasing voltage or a continuously decreasing voltage, wherein in case of a continuously increasing voltage the monotonically varying frequency modulation may be continuously increasing, and wherein in case of a continuously decreasing voltage the monotonically varying frequency modulation may be continuously decreasing. In an embodiment, the frequency modulation may be monotonically increasing, e.g. linearly increasing or monotonically decreasing, e.g. linearly decreasing to obtain a chirped pulse or pulse train compatible with first order dispersion compensation such that the chirped pulse may be compressed effectively in a relatively straightforward manner. Alternatively, the frequency modulation may be non-linearly increasing or decreasing in case a non-linearly chirped pulse or pulse train is desirable.

Figure 5:
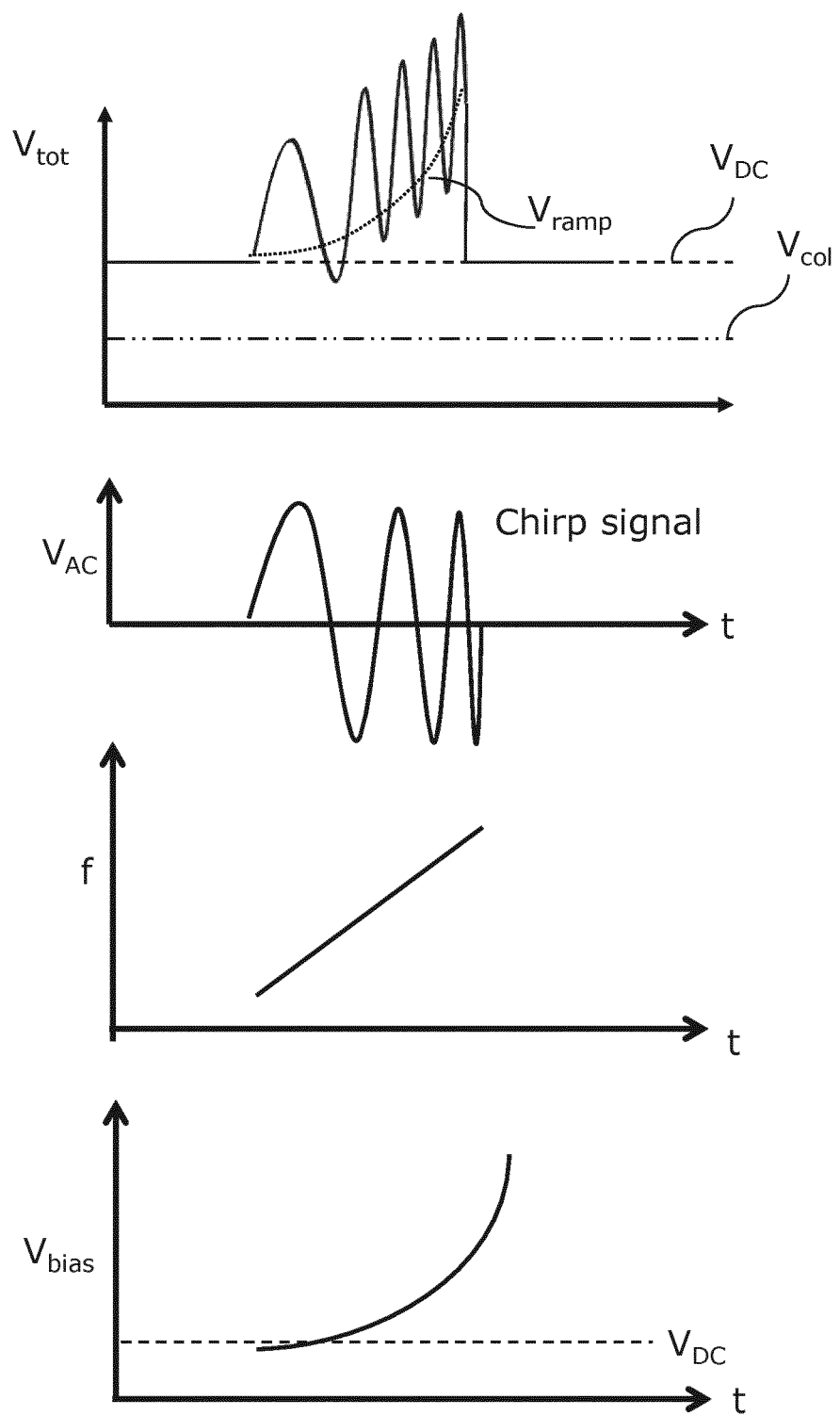
FIG. 5 schematically depicts various components of a voltage waveform applied to such a CMUT cell in a transmission mode of an ultrasound system according to an embodiment.

An example embodiment of the applied signals by the voltage source 45 is schematically depicted in FIG. 5, for the duration of a single pulse, in which the applied monotonically varying bias voltage is a continuously increasing bias voltage having a continuously increasing frequency modulation, that is a frequency modulation having a varying frequency that continuously increases, in order to obtain a chirped pulse or pulse train in which the low frequency spectral components are generated first in time. The bottom pane shows the DC voltage component as a function of time, the lower middle pane shows the applied frequency modulation, i.e. the applied alternating current component of the applied voltage, as a function of time and the upper middle pane shows the chirped voltage component $V_{AC}$ applied to the CMUT cells 100 operable in transmission mode, in which the increasing frequency of the frequency modulation of the applied voltage is immediately apparent. The top pane shows the overall voltage applied to the transmitting CMUT cells 100. Also indicated is the threshold voltage for collapse ($V_{col}$) of the membrane 114, which must at any time be well below the lowest voltage on the CMUT cells, e.g. at least 10%, preferably at least 20%, more preferably at least 30% below the lowest operating voltage applied to the transmitting CMUT cells 100 in order to operate the CMUT cells 100 in deep collapse mode as will be explained in more detail below. The mode of deep collapse is characterized in that the first CMUT membrane is kept in permanent contact with the floor of the CMUT cell by a sufficiently high bias voltage to compensate, at every instant, for the AC driving voltage that is applied during pulse transmission. This requirement is shown in the top pane of FIG. 5, where the lowest point of the total voltage is still higher than the collapse voltage ($V_{col}$).

The frequency modulated voltage may be applied to the appropriate CMUT cells 100 by a signal amplifier or other suitable voltage source 45 that generates the frequency-modulated voltage as a single signal. However, in an alternative embodiment the voltage source 45 may comprise two stages to generate different components of the frequency-modulated voltage, i.e. a first stage 102 for generating a static (DC) voltage component as indicated by the dashed line in the bottom pane of FIG. 5 and a second stage 104 for generating a variable voltage component including the frequency modulation, which signal typically is the difference between the overall voltage $V_{tot}$ and the aforementioned static component thereof. Other suitable embodiments of the voltage source 45 should be apparent, such as for instance an embodiment in which the voltage source 45 contains three discrete stages including a first stage for generating the static DC component ($V_{DC}$) of the CMUT drive voltage, a second stage for generating the variable DC component ($V_{ramp}$) of the drive voltage and a third stage for generating the frequency modulation of the signal ($V_{AC}$), e.g. a pulse circuit or the like. It is summarized that the voltage source 45 may be implemented in any suitable manner.

In an embodiment, the static component $V_{DC}$ of the applied voltage meets or exceeds the threshold voltage for forcing the CMUT cells 100 into their collapsed states. This has the advantage that the first stage 102 may include relatively large resistors and/or capacitors, e.g. smoothing resistors and/or capacitors, in order to generate a particularly low-noise static component of the overall voltage, which static component typically dominates the overall voltage such that the noise characteristics of the overall voltage signal will be dominated by the noise characteristics of this static component. As will be readily understood by the skilled person, the inclusion of such smoothing resistors renders the voltage generating stage unsuitable for generating alternating (AC) high-frequency components of the voltage; for instance, for a 1 MΩ smoothing resistor, the response of the resistor would be too slow, or example τ=0.1 ms for a CMUT cell 100 having a capacitance of 100 pF. In a preferred embodiment, the pulse width of the chirped pulses generated by the CMUT cells 100 is in the range of 0.1-1.0 μs, such that the 1 MΩ smoothing resistor would be at least two orders too slow. The voltage source 45 may combine the static and dynamic components of the voltage such that the frequency-modulated voltage may be applied over a single line to the CMUT cells 100. Alternatively, the different components of the applied voltage may be applied over separate lines to the CMUT cells 100.

At this point, it is noted that in FIG. 5 the frequency of the frequency modulation is varied linearly. In order to obtain optimal acoustic performance throughout this frequency range, it may be necessary to vary the voltage in a non-linear manner. It should be understood that in case a non-linear frequency variation in the frequency modulation is required, the voltage may be varied in a linear manner.

In an embodiment, the optimum output power or optimum sound pressure from the CMUT cell may be controlled by a feedback loop in which the instantaneous output intensity of the total (chirped, biased and ramped) signal is monitored. Such a feedback loop may be implemented as follows. During a first pulse, for a fixed pulse duration, for a certain first bias and slope of ramp the output of the CMUT cell is measured. This process is repeated by providing a subsequent second pulse, having an increased slope of the ramp, for which the output is measured again. If this subsequent output is higher than the initial output, this procedure is repeated again until for a later pulse the output intensity decreases, after which the next pulse will be produced with a decreased slope of the ramp.

This procedure may be applied during actual transmission ("on the fly") or in a separate calibration process. Measurement of the CMUT output may be done in the standard receive window between transmission pulses, where reflected sound is used. Alternatively, the transmission power may be inferred from the electrical input signal on the CMUT during transmission because at optimum efficiency, reflection of the driving electrical signal ($V_{AC}$) will be minimal.

Figure 6:
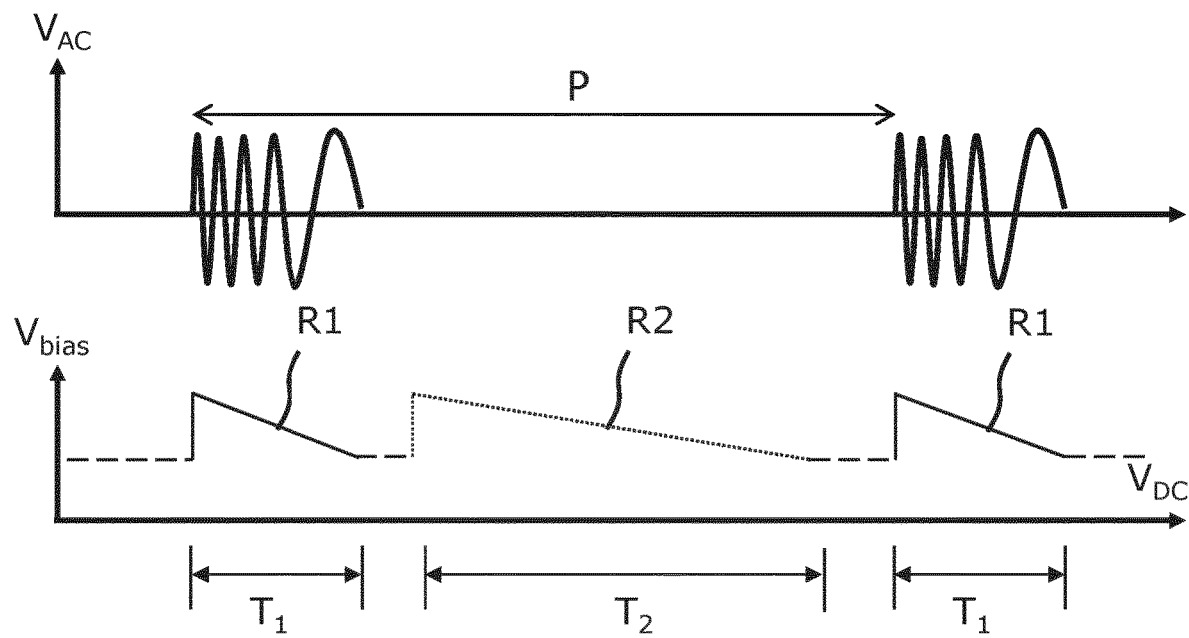
FIG. 6 schematically depicts various components of a voltage waveform applied to such a CMUT cell during a sequence of a first pulse transmission, subsequent reception and a second pulse transmission.

FIG. 6 schematically depicts . . . various components of a voltage waveform applied to such a CMUT cell during a sequence of a first pulse transmission, subsequent reception and a second pulse transmission. The CMUT cell is driven into the collapse mode by applying static VDC bias voltage. The bias voltage that drives the CMUT cells 100 into collapse is then varied (R1) in a lock-step manner with the $V_{AC}$ stimulus of the CMUT cells 100 for duration of T1 which corresponds to the total stimulus duration. Next the CMUT cells 100 receive the acoustic echoes for a period of $T_2$ during which the bias voltage can be adapted to vary sensitivity of the CMUT cells 100 to various frequency components in acquisition time (frequency gain compensation). The excitation period followed by the reception period are repeated at pulse repetition period indicated by P. The slope of the ramps R1 or R2 may be negative, as indicated in the figure, but equally may be positive.

Figure 7:
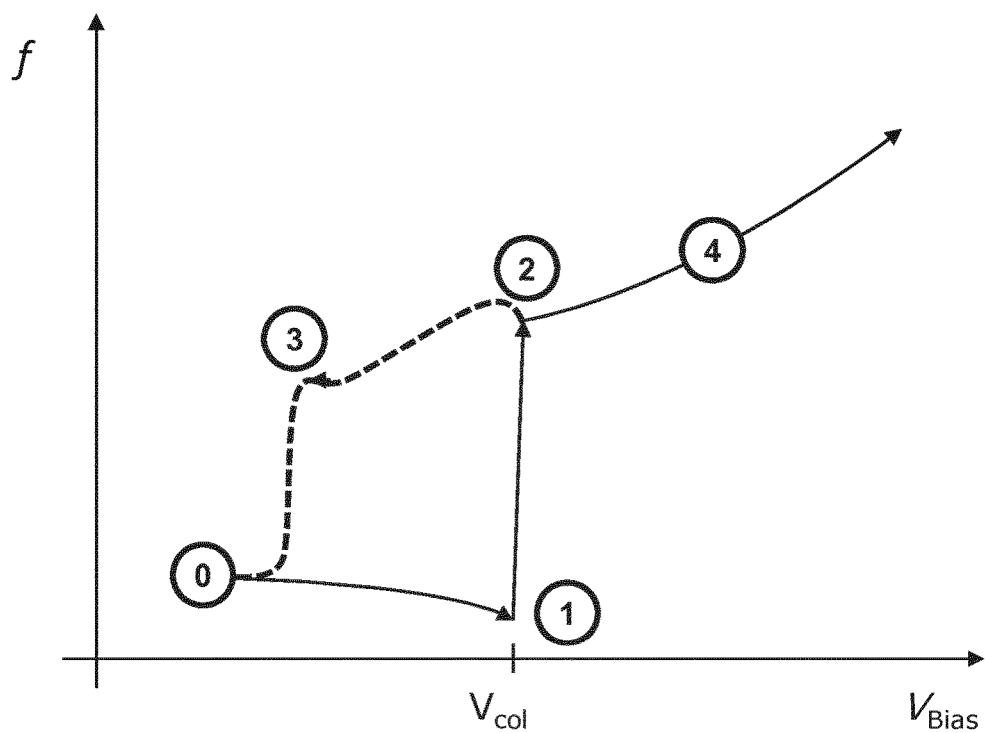
FIG. 7 schematically depicts the various operating regimes of a typical CMUT cell.

FIG. 7 schematically depicts the various operation regimes of a typical CMUT cell 100 in terms of membrane resonance frequency as a function of the applied bias voltage. Typically, a CMUT cell 100 can be operated in four distinguished modes of operation.

The first mode is sometimes referred to as the conventional mode, and is indicated by the region in between (0) and (1). In this operating regime, an increase in the bias voltage causes a decrease in the resonance frequency of the membrane of the CMUT cell, with the vibrating membrane 114 not contacting the ground electrode 122.

The second mode is referred to as the collapse mode and is indicated by the region at (2). The CMUT membrane enters the collapse mode when the total applied voltage exceeds the collapse voltage threshold ($V_{col}$). In this regime, the resonance frequency of the CMUT membrane 114 is substantially higher than in the conventional mode, and the vibrating CMUT membrane 114 gets into contact with the ground electrode 122. The region spans the range (3)→(4).

The third mode is sometimes referred to as the collapse-snapback mode and is indicated by the closed-loop region from (0)→(1)→(2)→(3)→(0). The resonance frequency in this mode of the membrane 114 is not well-defined as it changes throughout the whole cycle of conventional and collapse mode and snapback region. In this mode the vibrating CMUT membrane 114 comes in and out of contact with the ground electrode during its excitation.

The fourth mode is sometimes referred to as the deep-collapse mode and is indicated by the region (2)→(4) and beyond. In this mode, the resonance frequency of CMUT membrane 114 is as high or higher as in the collapse mode and increases with increase in bias voltage (typically about 0.1 MHz/V) and the vibrating CMUT membrane 114 stays in contact with the ground electrode 122 at any point in time.

It is important to note that strong hysteresis in the resonance frequency of the membrane 114 is typically observed when varying the bias voltage within the first three modes described above, as a result of which it complicates the reliable operation of the CMUT cell 100. In contrast, such hysteresis effects are minimal in the deep collapse mode. In at least some embodiments, the CMUT cells 100 are operated in the deep-collapse mode only, for instance when operating the CMUT cells 100 in an aqueous medium, e.g. water or a bodily fluid such as blood, in order to improve reliability by suppression of variable hysteresis effects.

Figure 8:
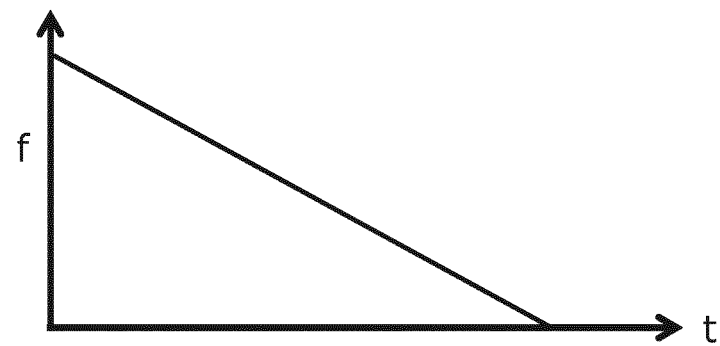
FIG. 8 schematically depicts various components of a voltage waveform applied to such a CMUT cell in a reception mode of an ultrasound system according to an embodiment.
Figure 8:
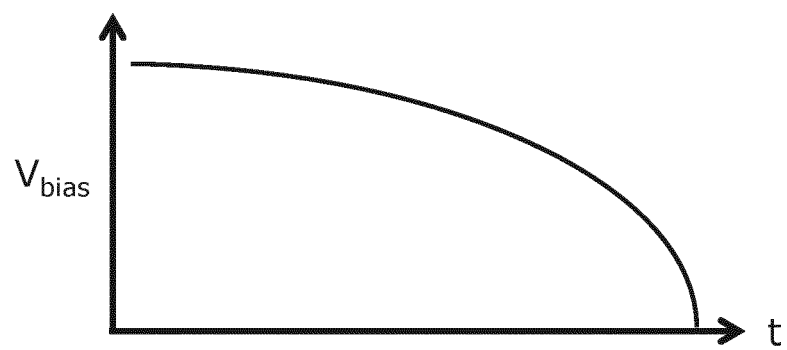

The bottom pane of FIG. 8 schematically depicts the waveforms applied by the voltage source 45 during a reception mode of an ultrasound diagnostic imaging system in an embodiment (this of course irrelevant for ultrasound therapeutic systems in which pulse echoes are not collected). In this embodiment, the receiving CMUT cells 100 are also forced into a collapsed state, for which the applied voltage may be the mirror image of the bias voltage applied in the transmission mode of the system, here a continuously decreasing bias voltage, in order to force the CMUT cells 100 operable in the reception mode through a spectrum of resonance frequencies as indicated in the top pane of FIG. 8. This for instance may be desirable in application domains where a chirped pulse is submitted into the medium to be imaged, as different pulse frequencies typically induce the reception of pulse echoes at different points in time due to their different depths-of-field, with high-frequency components typically arriving earlier due to their limited penetration depth, as is known per se. In an embodiment, the ultrasound diagnostic imaging system may include a user interface, which will be explained in more detail below, allowing the user to control the variation of the bias voltage in real-time. This for instance allows the user to select a particular resonance frequency of the CMUT cells 100 in accordance with a desired imaging mode of the system in order to obtain optimal sensitivity of the CMUT cells 100 at that imaging mode.

As previously explained, the probe of the ultrasound system may be adapted to transmit chirped pulses into the medium of interest in accordance with certain operation modes of the system, such as for instance ultrasound harmonic imaging or contrast imaging in case of an ultrasound diagnostic imaging system. However, in order application domains, such as for instance high-resolution ultrasound imaging, or ultrasound therapy, a short high-energy pulse with maximal frequency bandwidth is required to obtain the desired high resolution or high energy. In such application domains, it will be necessary to compress the chirped pulse or pulse train.

For instance, for a chirped Gaussian pulse, the following applies (note that the wave number is related to the wavelength via $k=2\pi/\lambda$). The amplitude of a chirped Gaussian pulse is represented by:

$$A(t)=\exp(-\gamma t^2)\exp(i\omega_0 t)$$

where $\gamma=\alpha-i\beta$ defines the envelope and chirp of the pulse, and the intensity is $$I(t)=|A(t)|^2=\exp(-2\alpha t^2)$$

where the pulse width $\tau_p=\sqrt{(2\ln 2)/\alpha}$ is defined at full width half maximum (FWHM). From the Fourier transform of the amplitude A(t), the power spectrum $\tilde{I}(\omega)$ of the pulse can be obtained:

$$\tilde{I}(\omega) = |\tilde{A}(\omega)|^2 = \exp\left[-(4\ln 2)\left(\frac{\omega-\omega_0}{\Delta\omega_p}\right)^2\right]$$

Such that with $\Delta\omega_p=2\pi\Delta f_p$, the following equation is obtained:

$$\Delta f_p = \frac{\sqrt{2\ln 2}}{\pi}\sqrt{\alpha[1+(\beta/\alpha)^2]}$$

The minimum time-bandwidth product for a pulse is then $$\Delta f_{min}\tau_{min} = \frac{2\ln 2}{\pi}$$

This states that there is a minimum bandwidth associated with a pulse of a certain (short) duration. If the pulse is chirped, its duration or pulse width is longer than the minimum value and it may be compressed by proper application of a dispersive material. If a pulse with initial pulse parameter $\gamma = \alpha - i\beta$ is propagated through a dispersive medium with group velocity dispersion:

$$k'' = \frac{d^2k}{d\omega^2}\bigg|_{\omega=\omega_0}$$

Then the optimum compression length (to get the shortest pulse) in this dispersive material is:

$$d_{opt} = \frac{-1}{2k''}\frac{\beta}{\alpha^2+\beta^2}$$

With minimum pulse width:

$$\tau_{min} = \tau_p\sqrt{1+(\beta/\alpha)^2}$$

As will be understood, the above analysis is well-known per se and applies to chirped pulses of Gaussian shape only; for other pulse shapes the appropriate equations are also well-known per se and will be immediately apparent to the skilled person.

Figure 9:
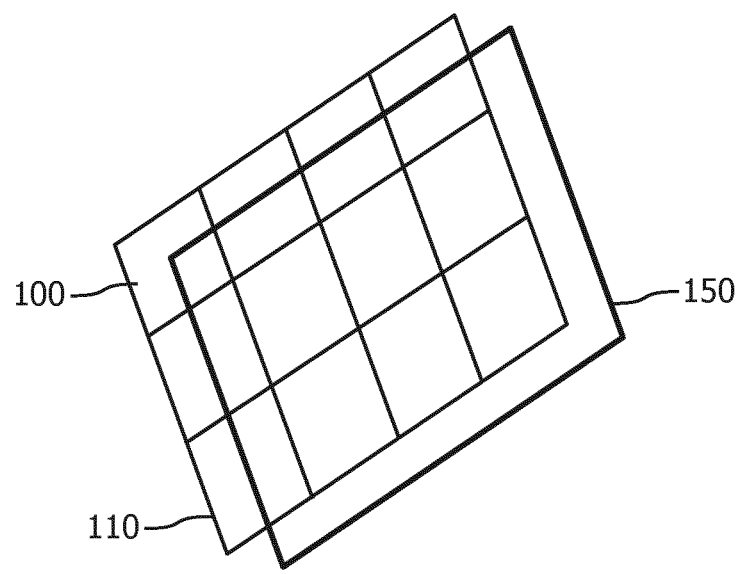
FIG. 9 schematically depicts an aspect of an ultrasound system according to an embodiment.
Figure 10:
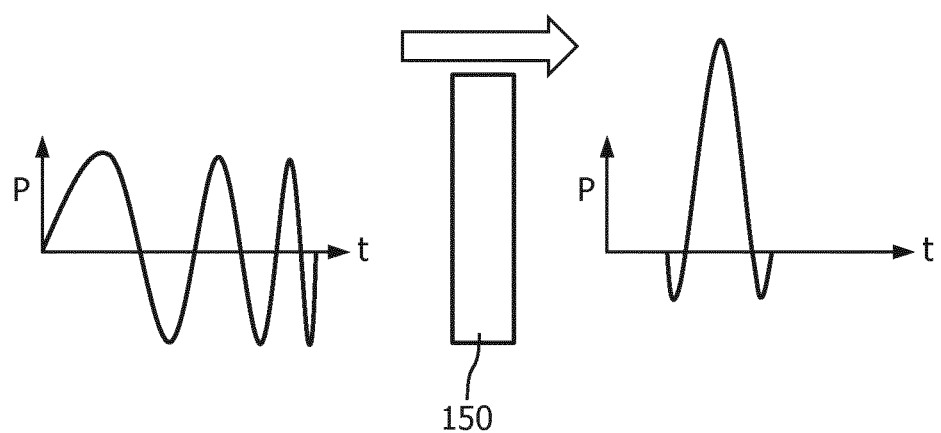
FIG. 10 schematically depicts an operating principle of the aspect of FIG. 7.

Therefore, in an embodiment, as schematically depicted in FIG. 9, the probe of the ultrasound diagnostic imaging system may further comprise a plate 150 of a dispersive material mounted in front of the transducer array 110 of CMUT cells 100 in order to compress the chirped pulse to the desired (minimal) pulse width such that during the transmission mode the chirped pulse or pulse train is transmitted through the plate 150 as schematically depicted in FIG. 10. The left hand signal indicates the chirped pulse and the right hand signal indicates the compressed pulse that is obtained after the chirped pulse has traveled through the dispersive medium of the plate 150, as indicated by the block arrow above the plate 150 in FIG. 10.

In an embodiment, the plate 150 is removably mounted in front of the transducer array 110 such that the plate 150 may be removed if the ultrasound diagnostic imaging system is to be used in applications for which chirped pulses are required as explained above. The plate 150 may be removably mounted in front of the transducer array 110 in any suitable manner, e.g. slotted into a receiving slot, clipped in front of the transducer array 110 using suitable clips or any other suitable fixation means that allow for the removal of the plate 150.

The plate 150 typically has a thickness that is matched to the chirp in the pulse or pulse train produced by the CMUT cells 100 in transmission mode in order to effectively compress the chirp towards its Fourier limit. The optimal thickness $d_{opt}$ of the dispersive material of the plate 150 may be obtained using well-known equations, such as for instance the following equation applicable to Gaussian pulses, which follows from the previously presented equations:

$$d_{opt} = \frac{-4\ln 2}{\omega_0^2 k''}\frac{f_0^2}{\Delta f_p^2}\sqrt{\left[\frac{\Delta f_p}{\Delta f_0}\right]^2 - 1}$$

The shortest obtainable pulse width for such a chirped Gaussian pulse therefore is:

$$\tau_{min} = \tau_p\frac{\Delta f_0}{\Delta f_p} = \frac{2\ln 2}{\pi\Delta f_p}$$

In the above, the group velocity dispersion expressed by $\omega_0^2 k''$ is material dependent as is well-known per se such that the thickness of the plate 150 is selected based on the dispersive characteristics of the material used. Any suitable dispersive material may be used for the plate 150. Particularly preferable materials are materials that have an acoustic impedance that is comparable to the acoustic impedance of water or biological tissue such that these materials have low reflective characteristics and induce negligible losses when used to image such media. For this reason, low-density polyethylene is particularly preferred. PEEK has similar acoustic impedance and is therefore also particularly suitable. However, many more suitable materials for the plate 150 will be immediately apparent to the skilled person.

It is noted for the avoidance of doubt that the sign of the chirp in the pulse or pulse train generated with the CMUT cells 100 is typically matched to the dispersive nature of the material of the plate 150. For instance, when using low-density polyethylene or PEEK, which exhibits anomalous dispersion characteristics, the low frequency components of the chirped pulse must be generated first as they take longer to travel through the dispersive medium. However, when using materials exhibiting normal dispersion characteristics, the sign of the chirp should be inversed, i.e. the high-frequency components of the chirp pulsed must be generated first, as is well-known per se.

It may be convenient to use a readily available material such as low-density polyethylene or PEEK for manufacturing the plate 150. However, in certain application domains it may be desirable to closely match the dispersive properties of the plate 150 to the chirp characteristics of the generated pulse, for instance to create a material having dispersive characteristics that are tuned to the frequency range of the generated pulse. In such a scenario, it may be desirable to engineer a material having the desired properties rather than to use a readily available material. The engineering of such purpose-built materials is known per se.

For instance, it is known to generate composite materials wherein the properties of the composite materials may be tuned by varying the composite material properties, e.g. varying composition, thickness and so on. Suitable composite materials for the plate 150 may include materials in which (micro) fibers or other (weakly) scattering particles such as carbon nanotubes, nanocrystals and the like are embedded in a polymer matrix. A particularly suitable example may incorporate glass fiber fragments in a silicone matrix, wherein the material properties may be tuned by varying the amount or density of glass fiber fragments in the matrix and/or by tuning the structure of the silicone polymers defining the matrix. In this respect it should be noticed that for a homogeneous material the acoustic impedance and acoustic velocity both depend on the bulk modulus and density of the material.

Another example of such engineered materials is acoustic metamaterials, which are artificially fabricated materials having an artificial lattice structure that are designed to control, direct, and manipulate sound waves. Such acoustic metamaterials may be tuned to exhibit the desired dispersive characteristics, e.g. by controlling material properties such as stiffness, which for instance may be controlled by controlling the degree of pattern repetition, i.e. the lattice constants, of the material, by selection of the materials used to create the acoustic metamaterials, and so on.

Yet another example of such engineered materials is microelectromechanical systems (MEMS) windows, which are typically constructed by centering a thin film of a material on a carrier, e.g. a thin dielectric film such as silicon nitride on a silicon carrier, wherein the material properties of the thin film such as material composition, stiffness and thickness may be controlled in order to provide the MEMS window with the desired properties.

In an embodiment, the CMUT cells 100 used to transmit the chirped pulse may also be used as a receptive channel for the pulse echo in the reception mode of the ultrasound diagnostic imaging system. In such a scenario, the pulse travels through the plate 150 twice, namely from the transducer array 110 towards the medium during transmission and as an echo from the medium towards the transducer array 110 during transmission. In this embodiment, the plate 150 may have a thickness of $0.5 * d_{opt}$ (i.e. half the optimal thickness for pulse compression) such that the chirped pulses are optimally compressed when received by the transducer array 110.

In order to obtain the optimal chirp and delays for driving the CMUT cells 100 in the transmission mode, the following procedure may be followed. First, determine the desired center frequency $\omega_0 = 2\pi f_0$ and determine the group velocity dispersion k" at this frequency. Second, determine the actual bandwidth $\Delta f_0$ at the center frequency, and from this, determine the minimum possible initial pulsewidth $\tau_p$ to calculate $\alpha$. Third, determine the potentially useful bandwidth $\Delta f_p$ and calculate $\beta$, the pulsewidth $\tau_{min}$ and the material thickness $d_{opt}$, and finally, fourth, determine the timing of the required voltage bias sweep for the CMUT cells 100.

It will be understood that the above explanation of chirp compression equally applies to an ultrasound therapeutic system in which chirped ultrasound pulses may be delivered to the tissue of a patient, wherein the tissue may comprise a tissue anomaly at a certain depth. In such applications, the depth of tissue may be considered as the dispersive plate 150 with the thickness of the plate corresponding to the depth of tissue. In such an embodiment, the chirp characteristics of the pulse generated by the CMUT transducer array 110 may be matched to the dispersive properties and path length of the tissue through which the pulse has to travel before it reaches the tissue anomaly, such that at the tissue anomaly the pulse has been compressed by the tissue through which the pulse has traveled to reach the anomaly in order to deliver a highly focused ultrasound pulse, i.e. focused in energy, to the anomaly. In other words, this maximises the peak power of the pulse delivered to the anomaly, thereby increasing the effectiveness of the therapy.

It is noted that it is of course equally feasible in such therapeutic applications to provide the ultrasound therapeutic system with an actual dispersive plate 150, wherein the desired compression of the chirped pulse is achieved by a combination of the plate 150 and the path through the tissue of the patient. This for instance may be advantageous if it is not straightforward to adjust the chirp characteristics of the pulse generated by the CMUT transducer array 110, in which case the effective compression of the pulse may be adjusted instead, for instance by matching the dispersive characteristics of the plate 152 the path length through the tissue such that the overall dispersion applied to the chirped pulse achieves the desired pulse compression.

Figure 11:
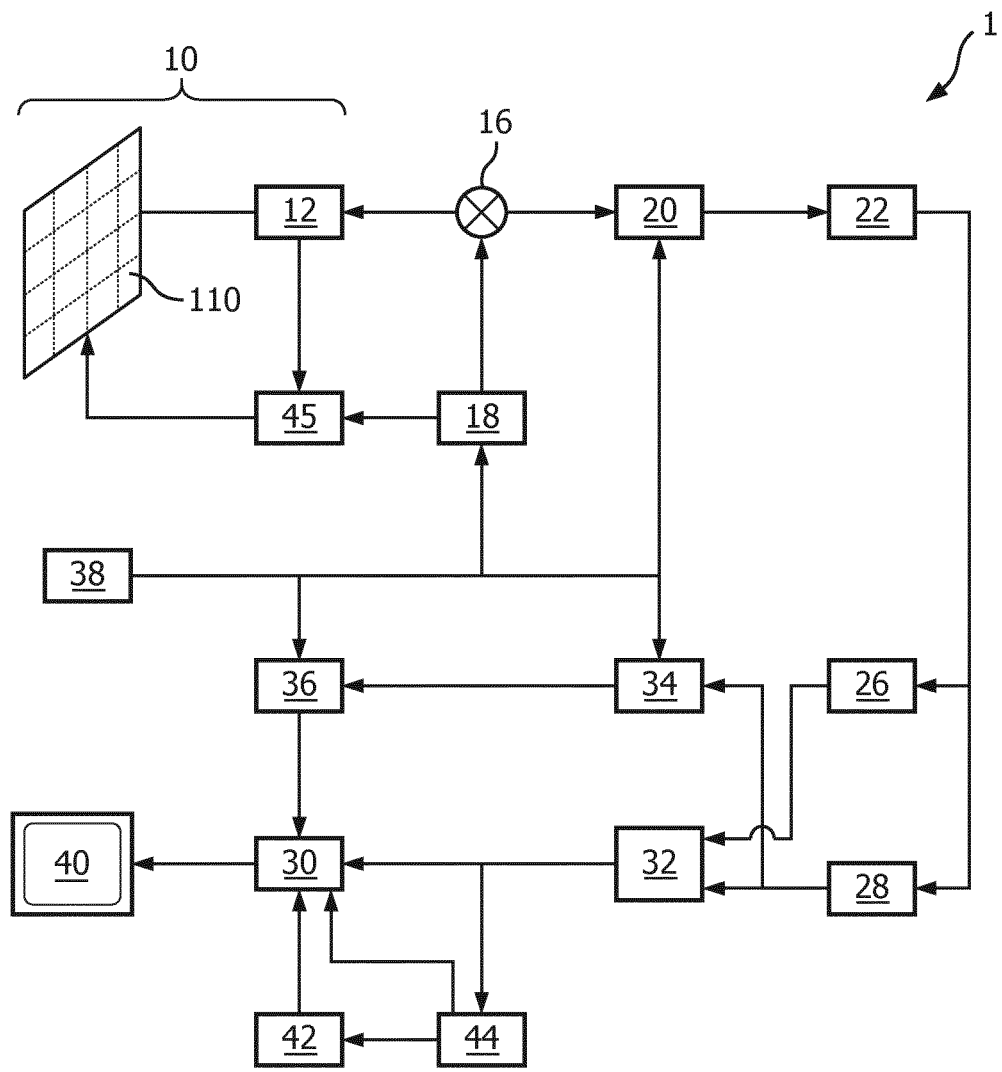
FIG. 11 schematically depicts an example embodiment of an ultrasound diagnostic system in block diagram.

In FIG. 11, an ultrasonic diagnostic imaging system with an array transducer probe according to an example embodiment of the present invention is shown in block diagram form. In FIG. 11 a CMUT transducer array 110 is provided in an ultrasound probe 10 for transmitting ultrasonic waves and receiving echo information. The transducer array 110 may be a one- or a two-dimensional array of transducer elements capable of scanning in a 2D plane or in three dimensions for 3D imaging.

The transducer array 110 is coupled to a microbeam former 12 in the probe 10 which controls transmission and reception of signals by the CMUT array cells. Microbeam formers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The microbeam former 12 is coupled by the probe cable, e.g. coaxial wire, to a transmit/receive (T/R) switch 16 which switches between transmission and reception modes and protects the main beam former 20 from high energy transmit signals when a microbeam former is not present or used and the transducer array 110 is operated directly by the main system beam former 20. The transmission of ultrasonic beams from the transducer array 110 under control of the microbeam former 12 is directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array 110, or at different angles for a wider field of view. The transducer controller 18 may be coupled to control the aforementioned voltage source 45 for the CMUT array. For instance, the voltage source 45 sets the DC and AC bias voltage(s) that are applied to the CMUT cells 100 of a CMUT array 110, e.g. to generate the chirped pulses in transmission mode as explained above.

The partially beam-formed signals produced by the microbeam former 12 are forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of CMUT transducer cells 100. In this way the signals received by thousands of transducer elements of a transducer array 110 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the transducer array 110 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 10 may not have 3D imaging capabilities and so on. Other variations will be apparent to the skilled person.

Figure 12:
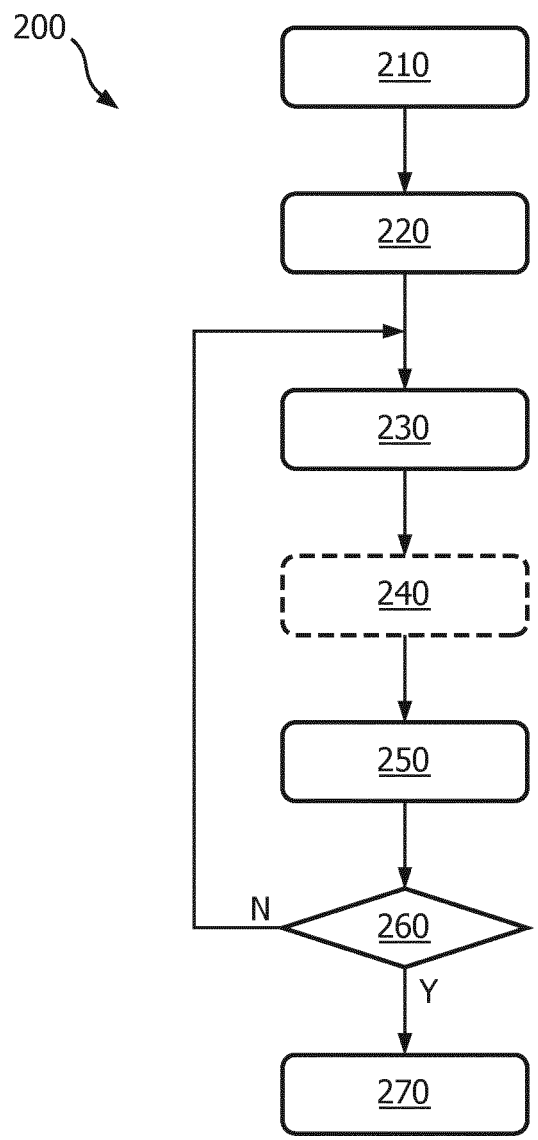
FIG. 12 is a flow chart of an ultrasound pulse generation method according to an embodiment.

FIG. 12 is a flow chart of an ultrasonic pulse generation method 200 employed by the ultrasound system according to embodiments of the present invention, such as the example embodiment of the ultrasound diagnostic imaging system 1 as shown in FIG. 11 or by the previously mentioned ultrasound therapeutic system. The method 200 starts in step 210 after which the method proceeds to step 220 in which a CMUT transducer array 110 is provided. In step 230, the CMUT transducer array 110 is driven by the voltage source 45 to generate the chirped pulse(s) in the transmission mode of the ultrasound system, e.g. the ultrasound diagnostic imaging system 1 as explained in more detail above, which chirped pulse(s) may be compressed, e.g. using plate 150, in optional step 240, which is typically applied when chirped pulses are undesirable, e.g. when the system 1 is used for high-resolution imaging. Alternatively, this compression step 240 may be applied by the tissue of a patient, optionally in combination with a dispersive played 150 as explained above, in case of an ultrasound therapeutic system.

Next, the method may proceed for an ultrasound diagnostic imaging system 1 by switching to a reception mode in step 250 in which the pulse echoes are received as previously explained, e.g. using a subset of CMUT cells 100 of the transducer array 110 not used for transmission or alternatively by operating the CMUT cells 100 previously used for transmitting the chirped pulses in reception mode, which received pulse echoes are processed for instance as explained above to generate the desired ultrasound image. As the processing of such ultrasound echoes is well-known per se, this will not be explained in further detail for the sake of brevity only. It suffices to say that any suitable ultrasound echo processing technique may be applied. In an embodiment, the reception mode of step 250 may comprise providing the CMUT cells 100 with a monotonically varying voltage in order to optimize the sensitivity of the CMUT cells 100 to different frequency components of the pulse echo arriving at different points in time, as has been explained in more detail above.

Subsequently, it is checked in step 260 is the imaging is complete; if not, the method 200 reverts back to step 230 for a next transmission/reception cycle; otherwise the method terminates in step 270.

At this point, it is noted that in addition to the aforementioned novel operation of the CMUT cells 100, it will be clear that additional advanced signal processing techniques may be used in both the generation of the excitation signal during transmission mode and signal reception in case of an ultrasound diagnostic imaging system. For instance, delays may be applied to different received echoes to compensate for the different transmission times of individual frequencies or a pulse compression technique may be used before image formation. Other suitable signal processing techniques that may be used in the context of the present invention will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound system comprising:
a probe including an array of CMUT (capacitive micromachined ultrasound transducer) cells, each cell comprising a substrate carrying a first electrode the substrate being spatially separated from a flexible membrane including a second electrode by a gap; and
a voltage source coupled to said probe and adapted to provide the respective first electrodes and second electrodes of at least some of the CMUT cells with a monotonically varying voltage including a monotonically varying frequency modulation in a transmission mode of said probe such that the CMUT cells are operated in a collapsed state and transmit at least one chirped pulse during said transmission mode.

2. The ultrasound system of claim 1, wherein the voltage source comprises:
a first stage adapted to generate a static component of said monotonically varying voltage during said transmission mode, wherein the static component is sufficient to force the CMUT cells in the collapsed state; and
a second stage adapted to generate a monotonically varying component of said voltage, said monotonically varying component including the monotonically varying frequency modulation, and wherein the voltage source is adapted to combine the static component and the monotonically varying component to form the monotonically varying voltage including the monotonically varying frequency modulation.

3. The ultrasound system of claim 1, wherein the monotonically varying voltage and the monotonically varying frequency modulation are monotonically increasing.

4. The ultrasound system of claim 1, wherein the monotonically varying frequency modulation is matched to monotonic variations in a resonance frequency of respective membranes of the CMUT cells induced by the monotonically varying bias voltage.

5. The ultrasound system of claim 1, wherein the monotonically varying frequency modulation is a linearly increasing frequency modulation.

6. The ultrasound system of claim 1, further comprising a plate of a dispersive material in front of the array of CMUT cells for compressing said chirped pulse.

7. The ultrasound system of claim 6, wherein the plate is removably mounted in front of said array.

8. The ultrasound system of claim 6, wherein the plate has a thickness of half an optimum thickness for said compression.

9. The ultrasound system of claim 1, wherein the at least one chirped pulse has a duration ranging from 0.1-1.0 microseconds.

10. The ultrasound system of claim 1, wherein the voltage source is further adapted to provide the respective first electrodes and second electrodes of at least some of the CMUT cells with a further voltage that forces the CMUT cells in the collapsed state during a reception mode of said probe.

11. The ultrasound system of claim 10, further comprising a user interface, wherein the voltage source is adapted to provide the further voltage as defined by a user using said user interface during the reception mode.

12. The ultrasound system of claim 1, wherein the ultrasound system is an ultrasound diagnostic imaging system or an ultrasound therapeutic system.

13. A method of ultrasonic pulse transmission, comprising:
providing an array of CMUT (capacitive micromachined ultrasound transducer) cells, each cell comprising a substrate carrying a first electrode, the substrate being spatially separated from a flexible membrane, including a second electrode by a gap; and
providing, in a transmission mode, the respective first and second electrodes of at least some of the CMUT cells with a monotonically varying voltage including a monotonically varying frequency modulation such that the CMUT cells are operated in a collapsed state and transmit at least one chirped pulse, preferably wherein the CMUT cells are operated in a deep collapse mode.

14. The method of claim 13, further comprising transmitting the at least one chirped pulse through a dispersive material to compress the at least one chirped pulse.

15. The method of claim 13, further comprising providing, in a reception mode, the respective first and second electrodes of at least some of the CMUT cells with a further voltage forcing the CMUT cells in the collapsed state.

* * * * *